US012319900B2

(12) United States Patent
Bongartz et al.

(10) Patent No.: US 12,319,900 B2
(45) Date of Patent: Jun. 3, 2025

(54) INTEGRAL GAS-INTRODUCTION AND STIRRING UNIT FOR GAS-LIQUID REACTORS

(71) Applicant: RHEINISCH-WESTFÄLISCHE TECHNISCHE HOCHSCHULE (RWTH) AACHEN, Aachen (DE)

(72) Inventors: Patrick Bongartz, Aachen (DE); Moritz Meyer, Pulheim (DE); Matthias Wessling, Aachen (DE)

(73) Assignee: RHEINISCH-WESTFÄLISCHE TECHNISCHE HOCHSCHULE (RWTH) AACHEN, Aachen (DE)

( * ) Notice: Subject to any disclaimer, the term of this patent is extended or adjusted under 35 U.S.C. 154(b) by 368 days.

(21) Appl. No.: 17/796,298

(22) PCT Filed: Jan. 29, 2021

(86) PCT No.: PCT/EP2021/052162
§ 371 (c)(1),
(2) Date: Jul. 29, 2022

(87) PCT Pub. No.: WO2021/152128
PCT Pub. Date: Aug. 5, 2021

(65) Prior Publication Data
US 2023/0087461 A1     Mar. 23, 2023

(30) Foreign Application Priority Data
Jan. 31, 2020   (DE) ................. 10 2020 102 420.7

(51) Int. Cl.
*C12M 1/04*       (2006.01)
*B01F 23/231*     (2022.01)
(Continued)

(52) U.S. Cl.
CPC ....... *C12M 1/04* (2013.01); *B01F 23/231244* (2022.01); *B01F 23/23314* (2022.01);
(Continued)

(58) Field of Classification Search
CPC ...... B01F 23/231244; B01F 23/23314; C12M 1/04; C12M 23/24; C12M 27/04; C12M 29/04
(Continued)

(56) References Cited

U.S. PATENT DOCUMENTS 6,708,957 B2 *   3/2004   Cote .................. C02F 3/201
                                                        210/636
2009/0034358 A1   2/2009   Bord et al.
2011/0165677 A1   7/2011   Brod et al.

FOREIGN PATENT DOCUMENTS

CN       108949558 A   * 12/2018
DE       2341180 A1      3/1974
(Continued)

OTHER PUBLICATIONS

Partial English Translation of WO 2007121958 A1 (Year: 2007).*
(Continued)

*Primary Examiner* — Charles S Bushey
(74) *Attorney, Agent, or Firm* — Renner, Otto, Boisselle & Sklar, LLP

(57) ABSTRACT

A gassing unit for bubble-free introduction of process gas into a liquid in a reactor, wherein the gassing unit includes at least:
  first and second spaced apart gas receiving chambers, the two gas receiving chambers connected to one another via at least two two-dimensional, gas-conducting diffusion membranes including hollow fibers spaced apart from one another and at least partially fixed to one another;

(Continued)

a gas supply receptacle on at least one gas receiving chamber;

a shaft receptacle on at least one gas receiving chamber; wherein the gassing unit for gassing the liquid in the reactor is supplied with process gas via the gas supply receptacle, is set into a rotational movement via the receptacle for the shaft and forms a convection flow within the reactor via rotational movement of the gassing unit in the liquid. Further included is a method for gassing a process liquid, a gas-liquid reactor including a gassing unit, and the use of a gassing unit for supplying biological cultures with process gases.

15 Claims, 8 Drawing Sheets

(51) Int. Cl.
 *B01F 23/233* (2022.01)
 *C12M 1/00* (2006.01)
(52) U.S. Cl.
 CPC ............ *C12M 23/24* (2013.01); *C12M 27/04* (2013.01); *C12M 29/04* (2013.01)
(58) Field of Classification Search
 USPC .................................................. 261/87, 104
 See application file for complete search history.

(56) References Cited

FOREIGN PATENT DOCUMENTS

| | | | |
|---|---|---|---|
| DE | 2431450 | A1 | 1/1975 |
| DE | 3122186 | A1 | 12/1982 |
| DE | 3544382 | A1 | 6/1987 |
| DE | 3809163 | A1 | 9/1988 |
| DE | 9000419 | U1 | 5/1990 |
| DE | 4142502 | A1 | 6/1993 |
| DE | 4404600 | C1 | 7/1995 |
| DE | 102004029709 | B4 | 5/2006 |
| DE | 102005053333 | A1 | 5/2007 |
| DE | 102005053334 | A1 | 5/2007 |
| DE | 102006008687 | A1 | 8/2007 |
| EP | 0172478 | A1 | 2/1986 |
| EP | 0226788 | A1 | 7/1987 |
| JP | S5482847 | A | 7/1979 |
| JP | H01147564 | A | 6/1989 |
| JP | 2009-514512 | A | 4/2023 |
| KR | 2012-0027552 | A | 3/2021 |
| WO | 2007051551 | A1 | 5/2007 |
| WO | WO 2007/121958 | A1 * | 11/2007 |

OTHER PUBLICATIONS

Partial English Translation of CN 108949558 A (Year: 2018).*
International Preliminary Report on Patentability corresponding with International Application No. PCT/EP2021/052162 Issued Jul. 28, 2022, with English translation.
Berthold Hambach, Der Einsatz von Wirbelschichtreaktoren in der Zellkulturtechnik—Beiträge zur Verfahrensentwicklung, Berichte des Forschungszentrums Julch; 2886, ISSN 0944-2952 Institut für Biotechnologie Jul-2886.
International Search Report for corresponding International Application No. PCT/EP2021/052162 mailed May 18, 2021 and English translation.

* cited by examiner

INTEGRAL GAS-INTRODUCTION AND STIRRING UNIT FOR GAS-LIQUID REACTORS

CROSS-REFERENCE TO RELATED APPLICATIONS

This application is a national phase of International Application No. PCT/EP2021/052162 filed Jan. 29, 2021, which claims priority to German Application No. 102020102420.7 filed Jan. 31, 2020, each of which is hereby incorporated herein by reference in its entirety.

BACKGROUND OF THE INVENTION

The reliable production of important basic materials via more sustainable production methods is nowadays increasingly in the focus of public interest. This approach not only concerns the production method as such, but also extends to the properties of the substances used after the planned period of use. This is particularly evident from the fact that for a large number of chemical classes synthesized from petroleum in recent decades, alternative and biological production variants are now increasingly being developed which, in addition to a more resource- and energy-efficient production process, are also expected to deliver improved chemical and biological properties, such as faster degradability, of the substances produced.

This approach is being pursued for surfactant biomolecules in particular, since these substances can have a lasting impact on the environment and the value added, for example in cosmetic or pharmaceutical products, allows the currently still higher production costs to be offset. A more environmentally friendly manufacturing alternative is based on fermentation processes of biological systems with renewable raw materials as nutrient media and under oxygen input. A disadvantage, however, is that in the biosynthesis of proteins and surfactants there is usually heavy foaming in the fermenters, which is detrimental to the performance and the overall process flow. Up to now, the method of choice for gassing these systems has been bubble gassing and subsequent breaking of the bubbles by means of a stirrer or the use of anti-foaming agents. This should ensure a bubble-free fermentation without loss of biomass. However, bubble gassing including bubble break-up is disadvantageous, since further control parameters complicate the control of the process and the mechanical foam destruction energetically increases the cost of the process. Foam inhibitors are not a sustainable alternative, since the additional purification in the downstream process flow strongly influences the process costs. In this respect, the existing fermentation methods and the equipment used for them need improvement to ensure a simple and reproducible fermentation process without foam formation.

Some approaches to bubble-free gassing of fermentation liquids can also be found in the patent literature.

For example, DE 10 2006 008 687 A1 describes a process for gassing liquids, especially in biotechnology and in particular cell cultures, with gas exchange via one or more immersed membrane surfaces such as tubes, cylinders or modules, characterized in that this membrane surface performs any rotationally oscillating movement in the liquid.

Furthermore, DE 44 046 00 C1 discloses a process for the bubble-free gassing of microorganisms immobilized in a reactor on a carrier material, wherein the carrier material with the microorganisms is flowed against by an aqueous solution which has been enriched with oxygen upstream of the carrier material via membranes to which an oxygen-containing gas is applied on one side.

In another patent document, DE 41 42 502 A1, a process for bubble-free introduction of hydrogen into aqueous liquids is disclosed, wherein the hydrogen is introduced into the aqueous liquid via a membrane. The process is characterized by using a membrane comprising a) a support structure formed of porous polymer, and b) at least one layer of non-porous polymer, wherein the aqueous liquid is in contact with the membrane on the side of the layer of non-porous polymer.

Such solutions, known from the prior art, can offer further potential for improvement, especially with regard to efficiency in the supply of process liquids with process gases and in particular with regard to reliable prevention of foam formation, even for systems with difficult product properties.

BRIEF SUMMARY OF THE INVENTION

It is therefore the task of the present invention to at least partially overcome the disadvantages known from the prior art. In particular, it is the task of the present invention to provide a gassing unit and a gas-liquid reactor with the same, which is characterized by a particularly efficient and uniform gas supply of process liquids, with a significant reduction of foam formation during the feed.

The task is solved by the features of the independent claims, respectively, directed to the gassing unit according to the invention, the gas-liquid reactor according to the invention, the process according to the invention and the use according to the invention. Preferred embodiments of the invention are described in the dependent claims, in the description or in the figures, whereby further features described or shown in the subclaims or in the description or in the figures may individually or in any combination constitute an object of the invention, as long as the context does not clearly indicate the contrary.

According to the invention, the task is solved by a gassing unit for the bubble-free introduction of a process gas into a liquid located in a reactor, wherein the gassing unit comprises at least:

a first gas-receiving chamber and, at spaced therefrom, a second gas-receiving chamber for receiving a process gas, the two gas-receiving chambers being connected to one another via at least two two-dimensional, gas-conducting diffusion membranes comprising hollow fibers which are spaced apart from one another and at least partially fixed to one another;

a receptacle for a gas supply on at least one of the gas receiving chambers;

a receptacle for a shaft on at least one of the gas receiving chambers;

wherein the gassing unit for gassing the liquid in the reactor can be supplied with process gas via the gas supply receptacle, can be set into a rotational movement via the receptacle for the shaft, and a convection flow can be formed within the reactor via the rotational movement of the gassing unit in the liquid.

Surprisingly, it has been found that the above design results in an extremely efficient and resilient gassing-stirrer combination, which is suitable for a wide range of gassing applications in a wide variety of (bio)reactors. The introduction of process gases into a process liquid takes place homogeneously and gently to a high degree. Due to the combination of a simultaneous gassing and stirring surface, particularly large amounts of process gas can be introduced uniformly into the liquid via the exchange surface. This results in particular from the fact that membrane exchange surfaces made of hollow fibers are used, which are always actively freed from diffusing process gas by the constant movement within the liquid. Thus, on the one hand, the hollow fiber membranes used in the design according to the invention make it possible to realize overall larger exchange surfaces than those known so far, and on the other hand, they are used even more efficiently than in prior art solutions, since the simultaneous movement of the gases shearing off at the surface of the membranes completely avoids diffusion blockage by adhering gas bubbles. Moreover, the design is so robust due to the central supply of the process gas and the uniform distribution of it over a gas receiving chamber that high velocities and thus strong convection currents can be generated via the firmly anchored hollow fibers. The combination of gassing and agitation also ensures that the hollow fibers are not only indirectly flowed over by the process liquid, but actively. No dead spaces are created in the module itself, which contributes to the efficiency of the feed and the uniformity of the liquid gassing. In addition, shearing keeps the bubble size small. Thus, even difficult fermentation tasks with living cultures can be handled, for example in the production of foam-promoting substances, since the uniformity of the feed, the sheer amount of gas and the control of the bubble size by simultaneous shearing, prevent bubble and/or foam formation in the liquid medium to a high degree. The gassing unit can also be constructed from any number of gassing units connected in series, which facilitates the cleaning and sterilization of individual modules and the design within an up-scaling to larger reactor volumes.

The present invention relates to a gassing unit for bubble-free introduction of a process gas into a liquid located in a reactor, wherein the gassing unit comprises at least:
- a first gas receiving chamber and, spaced therefrom, a second gas receiving chamber for receiving a process gas, the two gas receiving chambers being connected to one another via at least two two-dimensional, gas-conducting diffusion membranes comprising hollow fibers spaced apart from one another and at least partially fixed to one another;
- a receptacle for a gas supply on at least one of the gas receiving chambers;
- a receptacle for a shaft on at least one of the gas receiving chambers;
- wherein the gassing unit for gassing the liquid in the reactor can be supplied with process gas via the gas supply receptacle, can be set into a rotational movement via the receptacle for the shaft and can form a convection flow within the reactor via the rotational movement of the gassing unit in the liquid. Furthermore, the present invention relates to a method for gassing a process liquid, a gas-liquid reactor comprising a gassing unit according to the invention, and the use of a gassing unit according to the invention for supplying biological cultures with process gases.

The gassing unit according to the invention is suitable for the bubble-free introduction of a process gas into a liquid in a reactor. Process liquids in reactors can be simultaneously stirred and supplied with a process gas by the gassing unit according to the invention. This means that a process gas is introduced continuously or discontinuously at time intervals into the process liquid via the gassing unit. The introduction of the process gas increases the concentration of the process gas in the liquid in the reactor, at least temporarily and at the feed point. Possible process gases may include oxygen, nitrogen, carbon dioxide, carbon monoxide, hydrogen, or similar gases or mixtures thereof. Typically, the process gases form reactants for carrying out further chemical reactions in the process fluid. The structure according to the invention allows process gases to be fed into process fluids without bubbles. Bubble-free in the sense of the invention means, in particular, that the bubble size of the process gas is in a range in which the bubbles on the surface of the membranes are not visible to the naked eye or are only visible with great difficulty. For example, the bubble size can be in the order of a few micrometer. The design according to the invention prevents, in particular, the formation or deposition of a foam on the surface of the process liquid during the course of the process. The liquids in the reactor can be, for example, aqueous solutions, dispersions or emulsions. However, the entry is not limited to aqueous systems. Non-aqueous liquid systems can also be gassed without bubbles.

The gas supply unit comprises at least a first gas receiving chamber and, spaced therefrom, a second gas receiving chamber for receiving a process gas. A process gas can be fed into one of the two gas receiving chambers via a gas feed line and distributed uniformly therein. The gas receiving chamber forms a reservoir for the process gas and, in contrast to direct feeding into the membranes, can also compensate for possible pressure fluctuations. The process gas is then fed from this gas receiving chamber via the hollow fiber membranes into the second gas receiving chamber, where the distance between the two receiving chambers can be selected as a function of the reactor dimensions, the length and mechanical stability of the hollow fibers, the desired gas input and the desired flow mechanics. The gas receiving chambers as such can be made of metal or plastic, for example, and have rotational symmetry. The two gas receiving chambers also have receptacles for the hollow fiber membranes, the receptacles allowing independent fixation of each hollow fiber membrane. The receptacles for the hollow fiber membranes can, for example, consist of grooves in the surface of the gas receiving chamber, in which the hollow fiber membranes can be mechanically clamped or glued and thus connected to the gas receiving chamber in a gas-tight manner.

The two gas receiving chambers are connected to each other via at least two two-dimensional, gas-conducting diffusion membranes made of hollow fibers that are spaced apart and at least partially fixed to each other. The process gases are therefore not introduced into the liquid via the gas-receiving chambers, but via hollow fiber membranes which are connected to the two gas-receiving chambers in a gas-conducting manner. The hollow fibers are not used as such, i.e. individually. Several hollow fibers are arranged next to or behind each other, so that a flat membrane is formed from the arrangement of the hollow fibers. For further stabilization of the membrane, the individual hollow fibers can also be fixed against each other by further mechanical means. For example, the individual hollow fibers can be stabilized against each other in the form of a fabric with non-gas-carrying threads or fibers running perpendicularly or approximately perpendicularly to the hollow fibers. For example, preferably one, further preferably two, further preferably 3 fixations in the form of an inert polymer thread can be inserted per cm of hollow fiber membrane, the thread being passed alternately above and below the hollow fibers and fixing the hollow fibers against each other. Diffusion membranes or microfiltration membranes are membranes in which the gas first diffuses into the membrane and then into the process liquid after passing through the hollow fiber shell. The membranes can be dense or porous, with the porosity of the membrane being in a range that, with sufficient flow, prevents concentration polarization on the outside of the membrane—and associated outgassing of the gas to be introduced in the form of bubbles. Possible pore sizes of non-"dense" membranes can range from 20 nm to 20 μm. "Dense" diffusion membranes can have a multilayer structure. This allows additional layers to prevent the process fluid from entering the membrane or, if necessary, the back-diffusion of unwanted gases into the membrane. Furthermore, the layered composite structure ensures that an extremely thin film of dense material can be supported on a mechanically strong layer, such as porous PMP, which is the active layer, for example, of PMP, TMCTS or PDMS/silicone. This thin, dense layer is critical to the permeability of the gases used. The thinnest possible layer ensures high mass transfer. The ratio of mass transfer through the membrane and its thickness is reciprocal for dense membranes. However, a thin active layer is usually mechanically unstable and requires a carrier, a so-called support. A support that is as porous as possible represents a negligible resistance to gas entry into the process fluid. Hollow fibers that can be used can, for example, be made of PMP (polymethylpentene) and have an inner diameter of 0.2 mm and an outer diameter of 0.38 mm. It is also possible to use PDMS (polydimethylsiloxane)/silicone membranes with an inner diameter of about 0.3 mm and an outer diameter of about 0.5 mm. Preferably, to form a planar membrane arrangement from the individual hollow fibers, more than 50, further preferably more than 100, further preferably more than 500 hollow fibers are arranged next to or behind each other. A planar arrangement results in cases where preferably more than 40%, further preferably more than 50%, further preferably more than 60% of the area between two spaced apart, not directly adjacent hollow fibers is covered with further hollow fibers. Such a planar arrangement can be achieved, for example, by fixing hollow fibers with above-mentioned dimensions at a distance of greater than or equal to 0.05 mm and smaller than or equal to 2.5 mm, further preferably of greater than or equal to 0.1 mm and smaller than or equal to 1 mm, spaced from each other on the gas receiving chamber. The gas flows through the gas receiving chamber into the hollow fibers joined together to form membranes and, depending on the driving force, exits into the liquid phase on the outside of the fiber.

The gassing unit comprises at least two diffusion membranes. This means that starting from the gas receiving chamber not only one membrane of several hollow fibers with a continuous gas path extends into the process liquid to the second gas receiving chamber, but that at least two membranes of several hollow fibers spaced apart from each other are arranged at the first gas receiving chamber, which can supply the process liquid with gas via a separate gas path. Preferably, there may be more than 10, further preferably more than 50, and further preferably more than 100 individual membrane areas of arranged hollow fibers extending from the first gas receiving chamber into the process liquid.

The individual hollow fibers can be connected to the gas receiving chamber by mechanically clamping the hollow fibers in specially designed devices on the gas receiving chamber or by bonding the membranes to the gas receiving chamber as such. Preferably, the individual hollow fiber membranes can be bonded to the gas receiving chamber.

A receptacle for a gas supply is located on one of the gas receiving chambers. The gas receiving chamber can be supplied with process gas from outside via a supply line through the reactor. For this purpose, an external gas source can be fed via a hose or capillary system into the interior of the reactor to the gas receiving chamber. There, the hose or capillary can be connected to a receptacle of the gas receiving chamber designed for this purpose. This can be done in a gastight manner, for example, by means of a fitting. Preferably, metric flangeless flat bottom connecting elements with flangeless ferrule can be used as fittings. The fittings can, for example, be made of metal or of plastic, for example PEEK. The fitting may be arranged centrically or a-centrically on the gas receiving chamber, advantageously the fitting being arranged on a side facing the hollow fiber membranes on the gas receiving chamber. Depending on the mode of operation of the gas supply unit, either only one or both gas receiving chambers can be equipped with receptacles for a gas supply. In particular, it is possible that the gassing unit can be operated in two modes. On the one hand, the gas supply can be operated in a "cross-flow" mode or, alternatively, in a "dead-end" mode. In the "dead-end" mode, gas is only conveyed into a gas receiving chamber of the gassing unit. In this mode, no pickup is required for a discharge of the process gas that has not been introduced, for example at the other gas receiving chamber.

A receptacle for a shaft is located on one of the gas receiving chambers. For the input of the mechanical energy required to move the gas supply unit, one of the gas receiving chambers comprises a device for receiving a shaft. The shaft can be guided through the reactor and connected to a drive or a gearbox, which can set the shaft in a rotating motion. The rotating shaft also causes the gassing unit to rotate and can move the process fluid across the planar hollow fiber membranes. The movement of the shaft and thus of the gassing unit can be in only one direction or preferably in two directions. Thus, a constant or alternating direction of rotation of the gassing unit with different speeds can be realized.

The gassing unit can be supplied with process gas via the gas supply intake for gassing the liquid in the reactor, whereby the gassing unit can be set into a rotational movement via the intake for the shaft and a convection flow can be formed within the reactor via the rotational movement of the gassing unit in the liquid. Through the gas and the shaft intake, both mechanical energy and process gas can be transferred to the gassing unit. Through the hollow fiber membranes, process gas is released into the process liquid and through the rotary movement of the gassing unit, and here actually of the flat hollow fiber membranes, a directed flow is generated within the liquid in the reactor.

In a preferred embodiment of the gassing unit, the projections of the diffusion membranes onto the gas receiving chambers can have a circular arc geometry. For the formation of a uniform flow profile within the reactor liquid and for the uniform overflow of the individual hollow fibers within the gassing unit, it has proven to be particularly suitable that the individual hollow fibers are not arranged in a straight line, but rather spaced apart from each other both in longitudinal and transverse direction on the gas receiving chamber. Thus, within the framework of the planar design of the membranes, the result is not a straight but a curved surface of arranged hollow fibers. In addition to the improvement and uniformity of the flow profile, this design can also contribute in particular to improving the gas entry into the liquid by uniform shearing of the gas bubbles from the hollow fiber membrane surface. In particular, the occurrence of larger gas bubbles on the surface of the membranes can also be delayed or prevented altogether.

A possible embodiment of the circular arc geometry is shown in the figures. Preferably, the circular arc may have a curvature greater than or equal to $1\ m^{-1}$ and less than or equal to 100 m$^{-1}$, further preferably of greater than or equal to 5 m$^{-1}$ and less than or equal to 70 m$^{-1}$.

Within a further preferred embodiment of the gas supply unit, the receptacle for the gas supply and the receptacle for the shaft can be arranged at only one gas receiving chamber. In order to equalize the flow profile in the reactor, it has proven to be particularly advantageous that the gas intake and the connection for the drive shaft are arranged centrally on only one gas receiving chamber. Further preferably, both the gas and the shaft receptacles can be designed together, for example in the form of a hollow shaft, so that both receptacles are located within one connection on the gassing unit. This can help reduce the number of mechanical components on the gassing unit. Furthermore, this combination port can preferably be designed centrally on the gassing unit. Preferably, the gassing unit can be supplied with process gas and the necessary kinetic energy simultaneously via only one combined receptacle on one of the gas receiving chambers. This can keep the flow profile of the gassing unit particularly homogeneous and reduce the equipment connection effort. The latter can also contribute to improved cleanability and sterilizability of the gas supply unit.

Within a further preferred aspect of the gassing unit, the two gas receiving chambers may each be cylindrical in shape and interconnected by one or more mechanical supports. A rotationally symmetric, cylindrical geometry has been found to be particularly advantageous for forming the most efficient convection flow possible within most reactor geometries. By means of this design of the gas receiving chambers, very uniform and also strong flows can be reproducibly induced both within the gassing unit and in the reactor itself, which contributes to a particularly good supply of process gases to the process liquid. In addition to fixing the relative position of the two gas receiving chambers with respect to each other via the hollow fiber membranes, it has also proved advantageous to fix the relative position of the two gas receiving chambers with respect to each other via one or more mechanical supports. This measure can reduce synchronization and unwanted oscillations of the gassing unit under high speeds. Preferably, the support can be guided through the center of the two cylindrically designed gas receiving chambers. Such an embodiment can improve the flow profile within the gassing unit, and here in particular between the individual hollow fiber membranes.

According to a preferred characteristic of the gassing unit, at least one retaining disk can be arranged between the two gas receiving chambers on the mechanical support, which is designed to mechanically retain the diffusion membranes. For the formation of a mirror-symmetrical convection flow within a large number of different reactor geometries, it has proven to be particularly advantageous that a retaining disk is arranged between the two gas receiving chambers on the support, which mechanically contacts the hollow fiber membranes. The hollow fiber membranes can either be "loosely" fixed by the mechanical holding by the retaining disk, or they can be stretched or twisted out of the fall line by the retaining disk. In the former case, holding the hollow fiber membranes in place also allows greater mechanical forces to be realized, for example due to higher circulation speeds of the gassing unit, without the risk of damaging the membranes. More fragile hollow fibers can overall be used. In addition to the mechanical task of holding the membranes, however, the achievable flow geometry can also be influenced by means of the retaining disk. The individual hollow fiber membranes can be selectively deflected or twisted out of the geometry predetermined by the connection to the gas-receiving chambers. This deflection changes the planar geometry of the membranes and can cause special convection patterns in the fluid. In this way, the membranes can be adjusted to specific gassing tasks and reactor geometries.

In a preferred embodiment of the gassing unit, the mechanical support can be adapted to transport process gas out of the gas receiving chambers. To achieve the most compact design possible for the gas supply unit with improved supply to the unit in cross-flow operation, it has proved particularly suitable for the mechanical supports to be in the form of hollow shafts which can also convey process gas to and from the gas receiving chambers.

In a further preferred embodiment of the gas supply unit, the area ratio of the total hollow fiber cross-sectional area to the cross-sectional area of the gas receiving chamber can be greater than or equal to 5% and less than or equal to 45%. By means of the proposed design, compact gassing units can be provided which have a significantly larger process gas exchange area compared to the prior art solution. These large exchange areas show only a low tendency to bubble formation and also form a more favorable flow behavior of the gassing unit. The total hollow fiber cross-sectional area is calculated by multiplying the cross-section of a single hollow fiber by the number of fibers arranged on the gas receiving unit. The cross-sectional area of the gas receiving chamber results from the area of the gas receiving chamber supplied with process gas. In the case where the gas receiving chamber has a central or outer surface to which hollow fiber membranes cannot be attached due to lack of process gas supply, this surface does not contribute to the above ratio even though the gas receiving chamber includes this surface. Within a preferred embodiment, the area ratio may be greater than or equal to 7.5% and less than or equal to 20%, further preferably greater than or equal to 10% and less than or equal to 15%. Within these ratios of gassing exchange area and gas receiving chamber, large quantities of process gas can be introduced under homogeneous flow conditions.

In a further preferred embodiment of the gassing unit, the packing density of the diffusion membranes relative to the volume of the gassing unit, expressed as the surface area of the hollow fibers divided by the volume of the gassing unit, may be greater than or equal to 0.1 cm$^{-1}$ and less than or equal to 7.5 cm$^{-1}$. In this case, the total surface area of the hollow fibers can be calculated using the number and the surface area of the hollow fibers that is freely accessible to process fluids. In the case of cylindrical or non-cylindrical geometries, the total volume of the gassing unit is obtained via the volume of the gassing unit accessible to process liquids between the gas receiving chambers. Using the design according to the invention, very high active gassing areas can be accommodated in a small space, which, in addition to a high process gas flow in combination with simultaneous stirring, can also contribute to the efficient supply of very high reactor volumes. Preferably, the ratio can also be greater than or equal to 0.25 cm$^{-1}$ and less than or equal to 6 cm$^{-1}$, further preferably greater than or equal to 0.5 cm$^{-1}$ and less than or equal to 3 cm$^{-1}$.

Further according to the invention is a method for gassing a process liquid within a reactor, wherein the gas introduction is carried out via a gassing unit according to the invention. The process step of gassing a process liquid via a gassing unit according to the invention can have several process advantages. Large quantities of process gas can be provided homogeneously in the fluid volume in this process step, and the combination of stirring and gassing allows an introduction without or with only very small bubble sizes to be realized. Due to the direct contact with the fluid boundary and the immediate shearing of the bubbles from the membrane surfaces, diffusion inhibitions caused by a concentration polarization at the surface of the hollow fibers are avoided and, in contrast to stationary arrangements, a larger liquid volume is supplied in the reactor due to the uniform movement of all fibers. In particular, due to the controlled formation of a convection within this process step, dead zones in the reactor and within the gassing unit can be avoided.

In a preferred embodiment of the method, the rotational speed of the membrane surface at the outermost edge of the gassing unit may be greater than or equal to 0.1 m/s and less than or equal to 5 m/s. By means of the set-up according to the invention, even diffusion membranes that are inherently mechanically unstable can be operated under high shear rates in the liquid. Without being bound by theory, this results from the fact that the spaced hollow membrane surfaces are flowed through or over and thus absorb only part of the motion pulse of the liquid. Advantageously, this results in a stripping of the diffused process gas and a reduction of the mechanical stress. The speed of the gassing unit can be adjusted via the dimensions of the area of the gas-receiving chambers and via the rotational speed of the gassing unit as such. From the reference to the hollow fiber, which is farthest away from the center of the gassing unit, a maximum rotation speed for the hollow fibers results. Accordingly, hollow fibers lying further inside the gassing unit have a low circulation speed. Further preferably, the orbital velocity of the membrane surface at the outermost edge of the gassing unit can be greater than or equal to 0.25 m/s and less than or equal to 4 m/s, further preferably greater than or equal to 0.5 m/s and less than or equal to 3 m/s.

Further according to the invention is a gas-liquid reactor, wherein the gas-liquid reactor comprises at least an outer reactor shell, a drive unit, a gas supply and a gassing unit according to the invention. The reactor according to the invention is a gas-liquid reactor for bubble-free gassing of a process liquid with a process gas. A gas-liquid reactor in the sense of the invention is delimited by an outer shell, which can be made of steel or glass, for example, which forms a space in its interior which can be filled with a process liquid at different filling levels. In particular, the use in disposable reactors made of plastics such as PP, PC, PET, LDPE, EVA, PVDC and composite systems made of these plastics is also advantageously possible. In addition to the liquid as such, the process liquid may also comprise other components such as reactants, suspended cells or organisms, salts, pH regulators or other substances. The process liquid may, for example, be in the form of an aqueous solution, dispersion or emulsion. The gassing unit can be connected to a supply line for the process gas via the gas intake. The process gas can be present in a further reservoir, such as a gas bottle, and delivered in a controlled manner via control valves. By means of a control unit, the gas flow and the composition of the gas to the gassing unit can be adjusted. For example, by means of a gas valve, a transmembrane pressure between the inner side of the membranes of the gassing unit and the process liquid, for example in the form of a fermentation broth, on the outer side of the membrane can be adjusted. The gas input to the broth usually scales proportionally with the transmembrane pressure. If gas continuously flows over/through the membrane on the inner side, the operating mode "cross-flow" is set. Only temporary overflow of the membrane lumen in the sense of a "flush" is also possible; for this purpose, a gas valve is opened in the meantime in a "dead-end" operating mode. This is particularly useful if gases from the process, for example $CO_2$ in classical aerobic fermentations, enter the membrane along the concentration gradient and concentrate there. This concentration can lead to the reduction of the overall performance of the gas feed, since the partial gas pressure of the gas to be fed in is reduced and the driving force is less. In addition, condensed water that has entered the membrane through the pores can also be discharged in such a rapid/intermittent manner. A particularly noteworthy advantage of "dead-end" gassing is that stoichiometrically only those gas molecules are "introduced", i.e. used, which are also metabolized in the process. This is relevant with regard to the economic efficiency of a (bio)process. In addition to these minimum components, the reactor can of course also have other internals. For example, it is possible that further components such as sensors, feed and discharge lines, heaters and/or cooling devices are arranged inside the reactor. The heating or cooling devices can also be arranged outside the reactor.

In a preferred embodiment of the gas-liquid reactor, the reactor can have no further stirring unit in addition to the gassing unit. In order to form a particularly efficient flow profile with homogeneous mixing also of the process liquid located inside the gassing unit, it has proved suitable for the reactor not to have any further actively moving devices for generating a directed flow in the process liquid. In these cases, the process liquid can flow around the hollow fibers in a particularly directed manner, and a large part of the process gases diffusing out of them can be sheared off. Further active agitator units could disturb the symmetry of the achievable convection and lead to different gas input quantities per unit volume of process liquid.

Within a further preferred embodiment of the gas-liquid reactor, at least one flow breaker may be arranged between the reactor shell and a gas receiving chamber. In addition to a very symmetrical design of the convection flow, it may be useful to redirect the convection induced via the gas supply and stirring unit according to the invention by means of flow breakers in certain areas of the reactor. This can contribute to better adaptability to specific reactor geometries. The flow breakers can be located between the gassing unit and the reactor walls, as well as between the gassing unit and the reactor bottom and lid. Particularly preferably, at least one flow breaker can be fitted between the gas supply unit and the reactor lid. This flow breaker can also be disc-shaped. This flow breaker can help to prevent uncontrolled absorption of gas from the head gas space of the reactor, in particular in the case of high exchange areas and high circulation speeds of the gassing unit. In particular, coning of the process liquid in the direction of the gassing unit is effectively prevented. Preferably, a disk-shaped flow breaker can be introduced at a height which is greater than or equal to ¼ and less than or equal to ¾ of the distance top edge of the gassing unit to the liquid level.

Further according to the invention is the use of a gas-liquid reactor according to the invention for supplying process gases to biological cultures suspended in a process solution or adhering to the interior of the reactor or to the gassing unit. Biological cultures, for example in the form of bacteria or fungi, can in principle be propagated in bioreactors in two different ways. First, the organisms can be in solution, for example in the form of a suspension, or they can be adhered to surfaces. Cultivation as a biofilm can in principle take place on the walls of the reactor or on the gassing unit according to the invention. The latter is preferred according to the invention, since a more uniform supply of nutrients can be ensured under the dynamic gassing and agitation conditions. In this respect, higher yields and faster conversions can be achieved. The reactor design according to the invention has proven to be particularly suitable for the propagation of microorganisms in an aqueous fermentation medium. The reactor design according to the invention allows targeted and reproducible adaptable gas quantities to be introduced into the reaction medium, with only a very small part of the mixing of the entire reactor volume being impeded by the gassing unit. There are no dead zones with less mixing and the process gas demand, for example oxygen, can be distributed evenly and quickly throughout the entire volume of the process liquid. Microorganisms are living organisms which can be propagated within the reactor. For the further advantages of the process according to the invention, explicit reference is made to the advantages of the gassing unit according to the invention.

Further according to the invention is the use of the gas-liquid reactor for supplying oxygen to bacteria in a nutrient medium. In particular, the reactor according to the invention can be used to supply oxygen to bacteria within a nutrient medium. Bacteria in particular exhibit varying process gas requirements as a function of their growth phase in nutrient media. Homogeneous dispersion of the introduced oxygen and uniform distribution is particularly difficult in these cases, since the gassing system must have sufficient reserves to selectively introduce both low and high amounts of oxygen into the nutrient medium. In these cases, for example, the transmembrane pressure must be highly flexible so that low amounts can be introduced reproducibly and high amounts can be introduced without bubbling. An example of a bacterium that can be used is *Pseudomonas putida* (*P. putida*), a gram-negative rod-shaped bacterium that occurs in water, soil or on plants. In Germany, the laboratory strain *P. putida* KT2440 is classified as an S1 organism and has GRAS status. For industrial biotechnology, *P. putida* KT2440 is an extremely interesting organism, as it possesses a versatile metabolism as well as a pronounced tolerance to organic solvents. Furthermore, *P. putida* is a popular organism for heterologous expression of genes and has a high growth rate on glucose.

Within a further preferred aspect of the use, the biological cultures can be adapted to produce foam-forming substances. Foam-forming substances in particular, and among these especially biosurfactants, are particularly difficult to ferment in conventional reactors, since these surfactants naturally contribute to particularly strong foam formation. One example of a biosurfactant is rhamnolipids, which are surface-active molecules produced by biocatalysts. These biosurfactants have the ecological advantage that, unlike petroleum-based surfactants, they can be rapidly biologically metabolized and are therefore more environmentally compatible. These can be produced particularly advantageously in the reactor according to the invention with the gassing unit according to the invention. Other biosurfactants exist which are produced by various microorganisms. These include, among others, sophorolipids produced by yeasts. Sophorolipids belong to the glycolipids. Furthermore, there are biosurfactants that belong to the class of lipopeptides, such as surfactin, which is produced by *Bacillus subtilis*. Surfactin is mainly used in the medical field. These can be produced with very little or no foam using the gassing unit of the invention.

In a preferred embodiment of use, the membrane area of the diffusion membranes relative to the reactor filling volume, expressed as $cm^2$ membrane area divided by $cm^3$ reactor filling volume, may be greater than or equal to 0.05 $cm^{-1}$ and less than or equal to 1.0 $cm^{-1}$. Especially for cell cultivation in bioreactors and for the synthesis of biomolecules, the above ratio of membrane area to reactor volume has proven to be particularly advantageous. By means of this ratio, the different growth phases with significantly different amounts of biomass can be sufficiently supplied with process gas, whereby sufficient controllability of the input of process gas is also provided at the beginning of cell propagation. By means of this design, a very controllable amount of process gas can be fed in as required, and an adapted amount in later growth phases when the transmembrane bridges are sufficiently small.

BRIEF DESCRIPTION OF THE SEVERAL VIEWS OF THE DRAWINGS

Further advantages and advantageous embodiments of the objects according to the invention are illustrated by the figures and explained in the following examples. It should be noted that the figures are descriptive only and are not intended to limit the invention in any way.

DETAILED DESCRIPTION OF THE INVENTION

Figure 1:
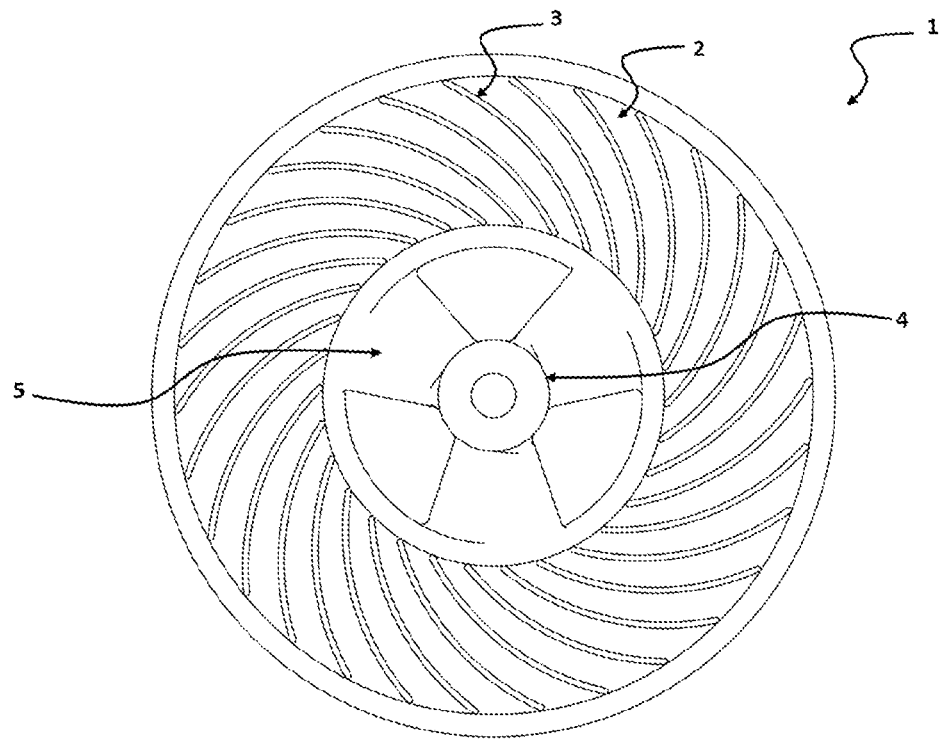
FIG. 1 is an embodiment according to the invention of a gas receiving chamber in a top view.

FIG. 1 shows a schematic top view of a gas receiving chamber 1. The gas receiving chamber 1 is cylindrical and is divided into an inner area, which comprises a receptacle for a process gas 4 and/or a receptacle for a shaft 4. Via this receptacle 4, the gas receiving chamber 1 is supplied with both process gas and mechanical drive energy. The process gas is conducted from the receptacle 4 via the trapezoidal connecting pieces 5 into the actual gas receiving chamber 1. The gas receiving chamber 1 shows a closed surface 2, which is provided with corresponding recesses 3 for receiving the diffusion membranes (not shown in this figure). The diffusion membranes in the form of hollow fibers can be clamped or glued into the recesses 3, and the diffusion membranes extend into the interior of the gas receiving chamber 1, so that a continuous gas-conducting path can be made from the receptacle 4, via the connecting pieces 5, into the actual interior of the gas receiving chamber 1 up to the hollow fiber membranes. The recesses 3 can also be referred to as the diffusion membrane fixation surface 3. The geometry of the diffusion membrane fixation surface 3 determines the planar configuration of the diffusion membranes. In this embodiment, the diffusion membrane fixing surface 3 has an arcuate configuration, with the consequence that the hollow fibers fixed in these recesses have in total a likewise arcuate membrane surface. The upper and lower gas receiving chambers 1 can have a mirror-image configuration. However, it is also possible that one of the two gas receiving chambers 1 does not have a receptacle for further process means. During operation, the gas receiving chambers 1 can be protected from direct access by process media by covers on the lower or upper side.

Figure 2:
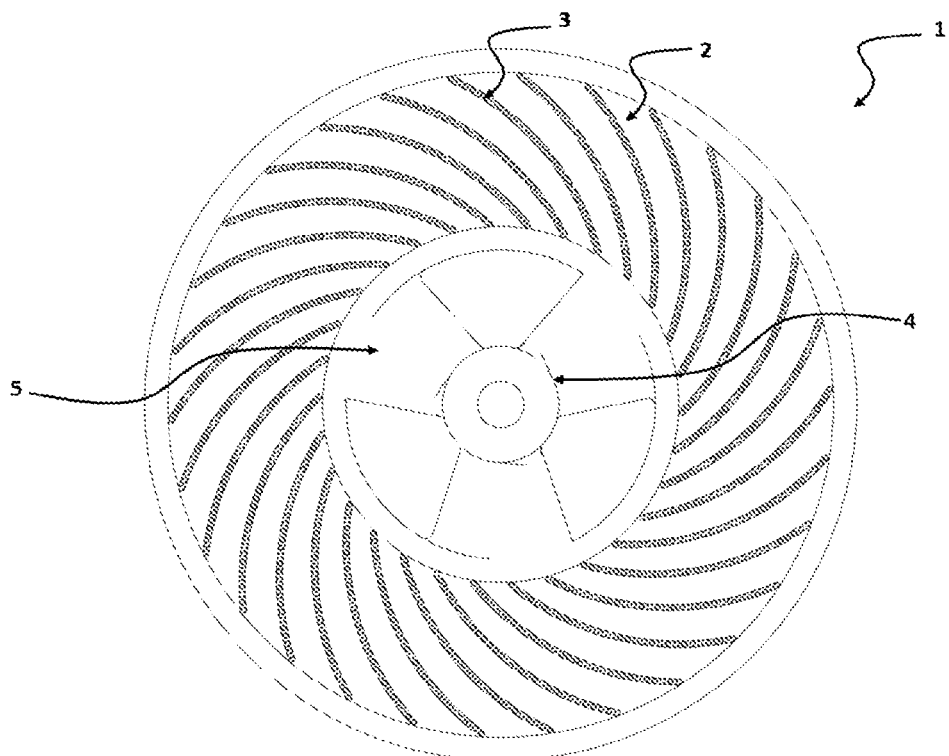
FIG. 2 is a further embodiment according to the invention of a gas receiving chamber in a top view.

FIG. 2 shows essentially the same arrangement compared to as FIG. 1 with the surface of the gas receiving chamber 2, the diffusion membrane fixing means 3, the receiving means for a process gas and/or a shaft 4, as well as the connection 5 of the gas receiving chamber with the gas receiving means 4. In contrast to FIG. 1, it is indicated at this point that individual cylindrical hollow fibers are inserted into the diffusion membrane fixing surface 3. Thus, it is made clear at this point that the surface is not a continuous flat membrane, but is formed from many individual hollow fibers that are offset from each other in both the X and Y directions so that they follow the arcuate configuration of the diffusion membrane fixation surface 3. In this respect, an arcuate geometry results for the diffusion membranes. In addition to the fixation of the hollow fibers in the two gas receiving chambers 1, the individual hollow fibers can also be mechanically fixed against each other (not shown in this figure). This additional fixation can be achieved, for example, by means of fibers woven or braided into the membrane perpendicular to the axis of symmetry of the hollow fibers. Thus, a lattice of hollow fibers and the fibers of the additional fixation is formed, which can be adjusted to the necessary mechanical load capacity of the diffusion membranes as a function of the number of further fixation points and as a function of the mechanical properties of the additional fibers.

Figure 3:
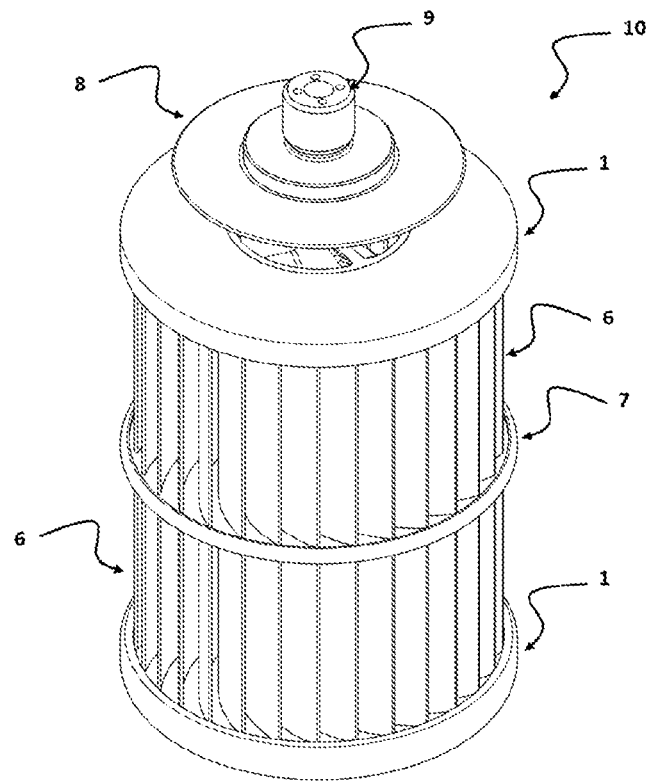
FIG. 3 is a side perspective view of an embodiment according to the invention of a gassing unit.

FIG. 3 shows an embodiment of a gas supply unit 10 according to the invention. In this figure, the entire gas supply unit 10 can be seen. The gas supply unit 10 is supplied with the process media process gas and energy via a supply line 9. The supply line opens into the receptacle 4 for the gas supply/shaft of the first gas receiving chamber 1 (not shown). The gas receiving chamber 1 is provided with a top cover at this point. Extending from the gas receiving chamber 1 are the individual diffusion membranes 6, which extend in total from the first gas receiving chamber 1 (shown here at the top) to the lower gas receiving chamber 1. In this figure, the planar design of the diffusion membranes 6 can be seen in particular, which is achieved by a specific arrangement of hollow fibers. The diffusion membranes 6 extend from the first to the second gas receiving chamber 1 and are held in place in the center by a retaining disc 7. Thus, between the gas receiving chambers 1, the gas conduction of the individual diffusion membranes 6 is not interrupted. The diffusion membranes 6 can either only be held by the retaining disk 7, deflected from their original position or mechanically tensioned. The retaining disk 7 can thus change the orientation of the individual diffusion membranes 6, which of course exerts an influence on the achievable convection of the gassing unit 10. In this figure, a flow breaker 8 is also shown, which is arranged above the gassing unit 10 in the direction of the reactor head space. This flow breaker 8 is optional and can prevent vortex formation in the reactor liquid, especially at very high rotation speeds of the gassing unit 10. This can contribute to a further reduction in bubble formation.

Figure 4:
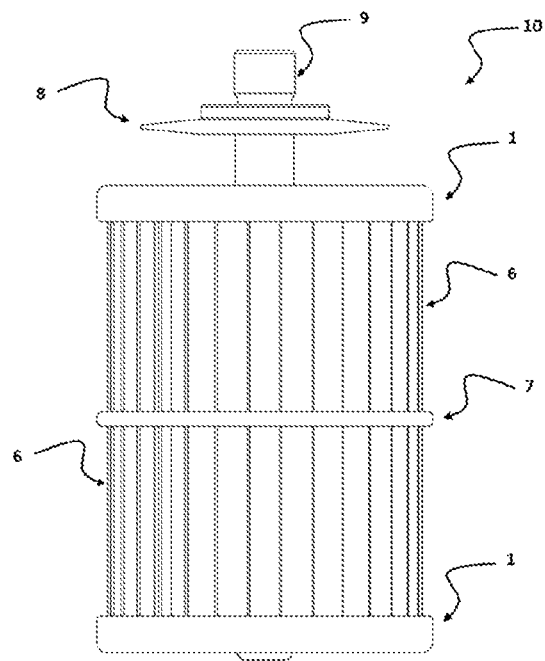
FIG. 4 is a front view of an embodiment according to the invention of a gassing unit.

FIG. 4 shows a front view of a gas supply unit 10 according to the invention. The gas supply unit 10 is supplied with the process media process gas and mechanical energy via a supply line 9. The supply line opens into the receptacle for the gas supply/shaft of the first gas receiving chamber 1 (not shown). Extending from the gas receiving chamber 1 are the individual diffusion membranes 6 which extend in total from the upper 1 to the lower gas receiving chamber 1. The diffusion membranes 6 extend from the first 1 to the second gas receiving chamber 1 and are held in place at the center by a retaining disk 7. In this figure, a flow breaker 8 is also shown, which is arranged above the gassing unit 10 in the direction of the reactor head space.

Figure 5:
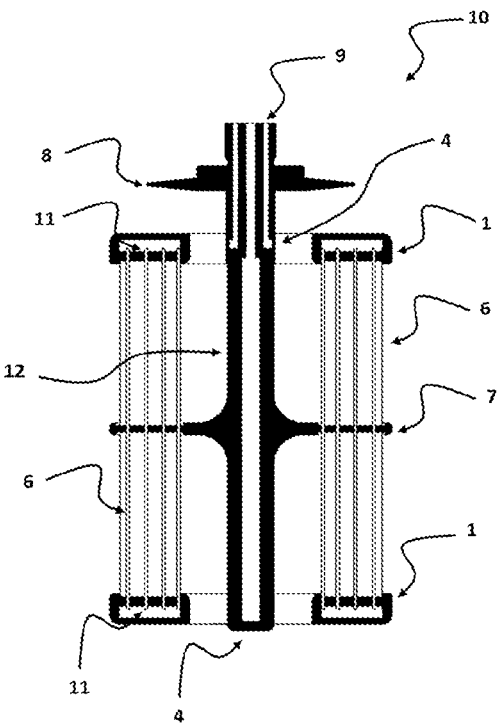
FIG. 5 is a schematic cut through a gassing unit according to the invention.

FIG. 5 shows an example of the media feed within a gas supply unit 10 according to the invention. The gas supply unit 10 is driven by a hollow shaft 9, which is connected to the gas receiving chamber 1 at the receptacle 4 for the gas supply/shaft. The shaft transports both the mechanical energy and the process gas to the gas receiving chamber 1. Via the receptacle 4 for the gas supply and the connection gas receptacle interior-gas receptacle, the gas is led into the interior gas receptacle 11. The individual hollow fiber membranes 6 are arranged on the gas receiving chamber 1 so as to extend into the inner gas receiving chamber 11. The hollow fiber membranes are thus supplied with process gas through the inner gas receiving chamber 11, which is conducted through the hollow fibers of the diffusion membranes 6 into the other gas receiving chamber 1. The process gas can pass from the hollow fibers of the diffusion membranes 6 into the process liquid, thus supplying the liquid with process gas. Both gas receiving chambers 1 are thereby additionally connected to each other via a mechanical support 12. This support can be used for other technical functions in addition to purely mechanical support. In this embodiment, the second (lower) gas receiving chamber 1 also comprises a receptacle 4 for the process gas. The process gas that has not diffused out of the membranes 6 is guided out of the gassing unit 10 via the support 12 in the form of a hollow shaft. The gassing unit 10 is thus operated in a "cross-flow" mode. In general, the process gas can be discharged as well as supplied via a central hollow shaft 12, which can also act as a mechanical support. In particular, the latter design can reduce the number of necessary connection points.

Figure 6:
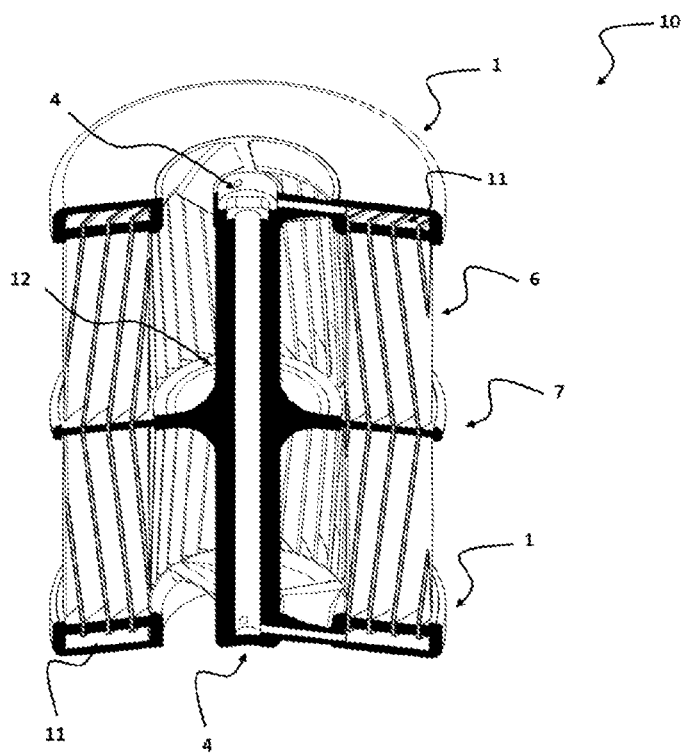
FIG. 6 is a cut through a gassing unit according to the invention.

FIG. 6 shows, also like FIG. 5, the media flow within a gas supply unit 10 according to the invention. The gas supply unit 10 is supplied with process gas and/or mechanical energy by the receptacle 4. The receptacle 4 is connected to the gas receiving chamber 1, whereby the process gas is fed into the inner gas receiving chamber 11. The individual hollow fiber membranes 6 are disposed on and extend into the gas receiving chamber 1. Thus, the hollow fiber membranes 6 are supplied with process gas through the inner gas receiving chamber 11, which is conducted through the hollow fibers of the diffusion membranes 6 into the other gas receiving chamber 1. The process gas can pass from the hollow fibers of the diffusion membranes 6 into the process liquid, thus supplying the liquid with process gas. Both gas receiving chambers 1 are thereby additionally connected to each other via a mechanical support 12, which can optionally also guide process gas. In this embodiment, the second (lower) gas receiving chamber 1 also comprises a receptacle 4 for the process gas. The process gas that has not diffused out of the membranes 6 is guided out of the gassing unit 10 via a gas line in the mechanical support 12. In this embodiment, the gassing unit 10 can be operated in a "cross-flow" mode. In general, therefore, the supply 4 as well as the discharge of the process gas can be effected via a central mechanical support 12 in the form of a hollow shaft. In particular, the latter design can reduce the number of necessary connection points.

Figure 7:
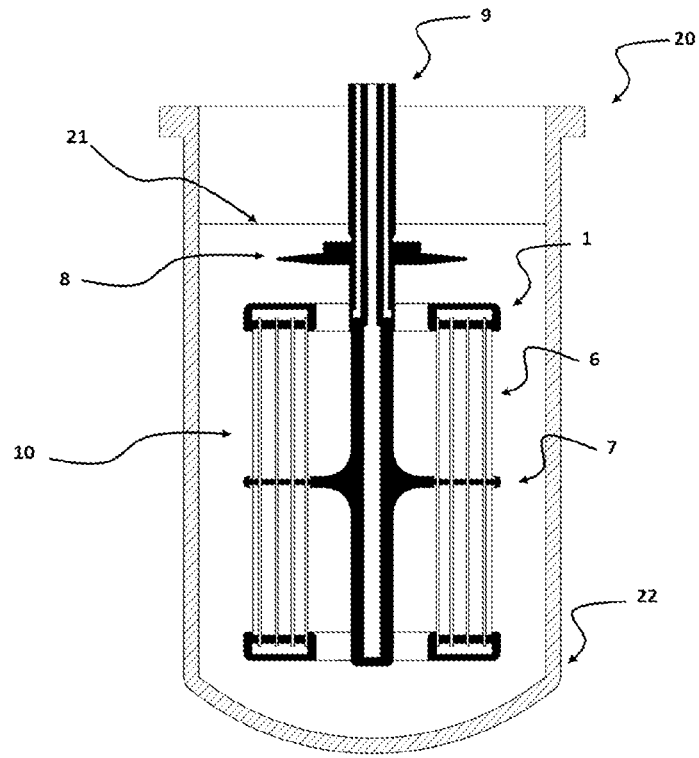
FIG. 7 is a schematic cut through a reactor according to the invention with a gassing unit according to the invention.

FIG. 7 shows a bioreactor 20 according to the invention with the gassing unit 10 according to the invention located therein. The reactor 20 is filled with a process liquid, the process liquid being present in the reactor 20 up to the process liquid level 21. The gassing unit 10 is held in and moved through the reactor 20 by the process gas/mechanical energy supply in the form of a hollow shaft 9. The further construction of the gassing unit 10 can be taken from the description for FIG. 5. It is also possible that further flow breakers or conductors 8 are arranged on the reactor walls 22 or in the liquid volume of the reactor 20 (not shown in this figure), whereby the convection of the process liquid can be influenced with this further flow breaker 8.

Figure 8:
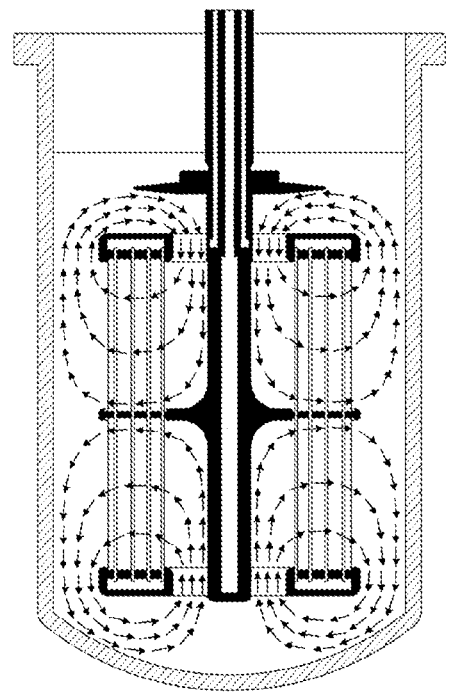
FIG. 8 is a schematic front view of a reactor according to the invention with a gassing unit according to the invention, including a possible convective flow profile.

FIG. 8 shows one possibility for the design of a reactor 20 according to the invention with a gassing unit 10 according to the invention. In this figure, one possibility for the formation of convection flows within the reactor 20 is shown. The convection flows result from a simulation of the flow behavior as a function of the geometry of the reactor 20 and the gassing unit 10. In this figure, it can be seen that the gassing unit 10 leads to the formation of a very symmetrical convection flow, whereby the interior of the gassing unit 10 in particular is also actively flowed around by the process liquid. In particular, the latter can contribute to a particularly efficient introduction of process gas through the diffusion membranes 6 into the process liquid. The convection of the process liquid around the individual hollow fibers 6 in particular forms small gas bubbles, which are sheared off the surface of the hollow fibers 6 and can thus supply the process liquid with process gas. This also ensures that the bubble size on the surface of the hollow fibers is kept small.

Figure 9:
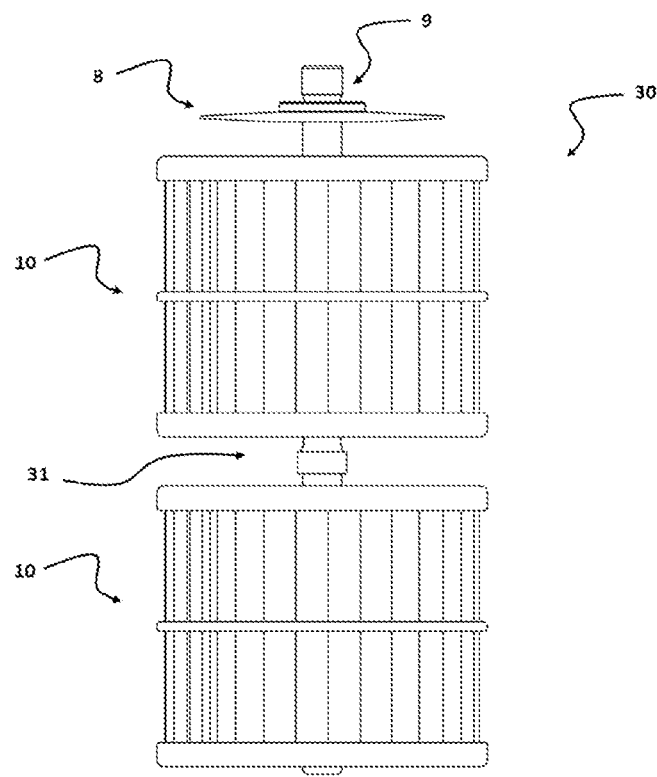
FIG. 9 is a schematic front view of a gassing unit according to the invention consisting of two gassing units connected in series.

FIG. 9 shows a serially connected gassing unit 30 consisting of two individual gassing units 10, which are coupled via a module coupling 31. Via the module coupling 31, both the process gas and the mechanical movement are transferred from the upper gassing unit 10 to the lower gassing unit 10. By interconnecting several gassing units 10, different reactor geometries and also sizes can be supplied with process gas very efficiently. The result is a design with as few connections as possible and a reliably predictable convection flow. This means that up-scaling to larger reactors 20 can easily be carried out, especially via series-connected gas supply units 30.

Figure 10:
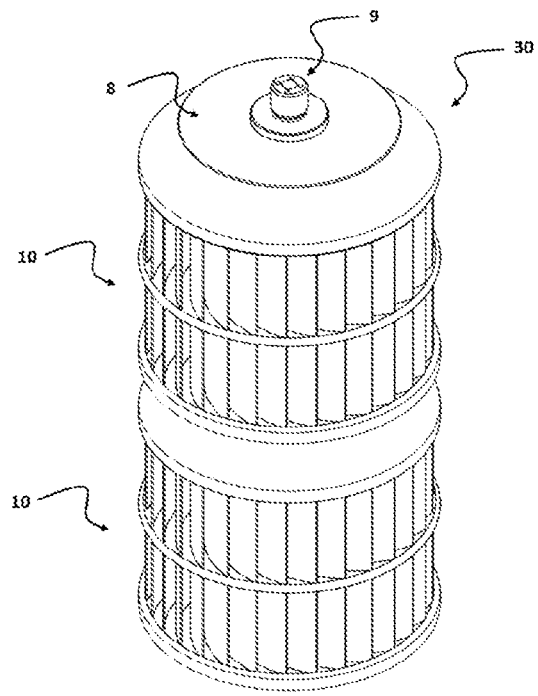
FIG. 10 is a schematic side perspective view of a gassing unit according to the invention consisting of two gassing units connected in series.

FIG. 10 shows the embodiment of FIG. 9 from another perspective.

Figure 11:
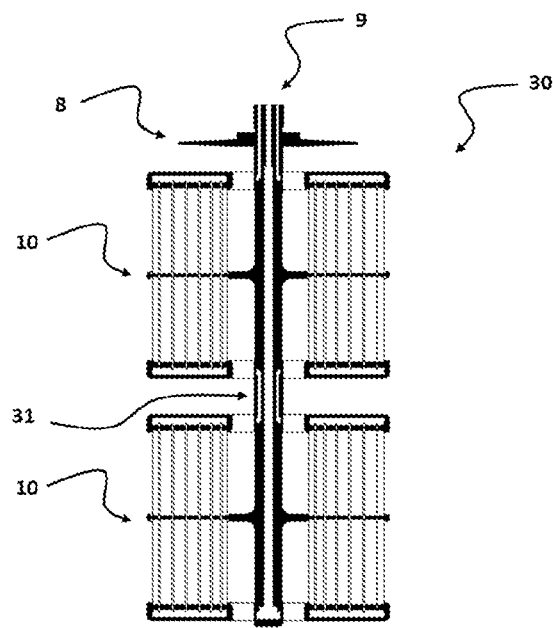
FIG. 11 is a schematic front view of a gassing unit according to the invention consisting of two serially connected gassing units with media supply.

FIG. 11 shows an example of the media feed within an arrangement of two gassing units 10 connected in series. The gassing unit 10 is driven by a hollow shaft 9, which is connected to the gas receiving chamber 1 at the receptacle for the gas supply/shaft 4. Via the receptacle for the gas supply 4 and the connection gas receptacle inner chamber 5, the gas is fed into via the individual hollow fiber membranes 6 into the other gas receptacle chamber 1. From this second gas receiving chamber 1, the remaining process gas can pass into the second gassing unit 10 via a module coupling 31. The module coupling 31 between the two gas supply units 10 enables both the transfer of the process gas and the transfer of the mechanical drive energy between the individual gas supply units 10.

Figure 12:
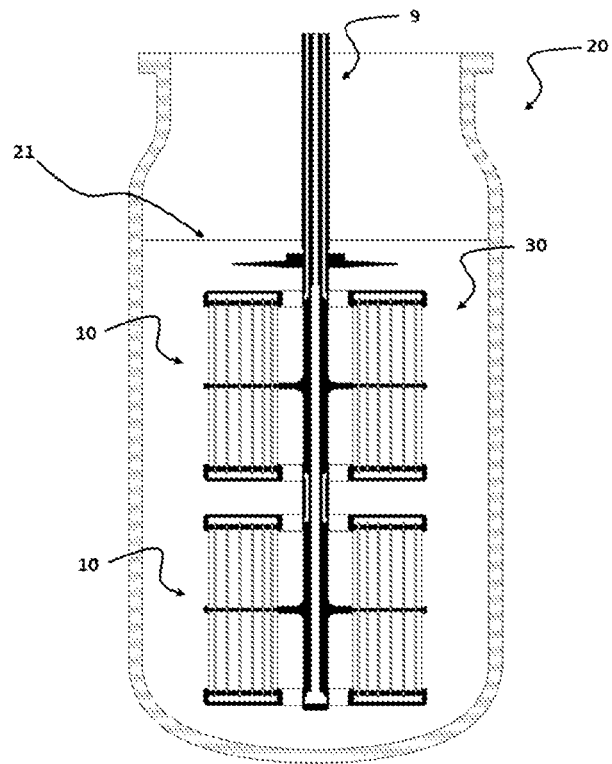
FIG. 12 is a schematic front view of a reactor according to the invention with two serially connected gassing units according to the invention with media supply.

FIG. 12 shows an embodiment of a reactor 20 according to the invention with two gassing units 30 connected in series, which consist of two individual gassing units 10. By connecting several gas supply units 10 in series, reactors 20 with a large aspect ratio in particular can also be reliably supplied with process gas.

Figure 13:
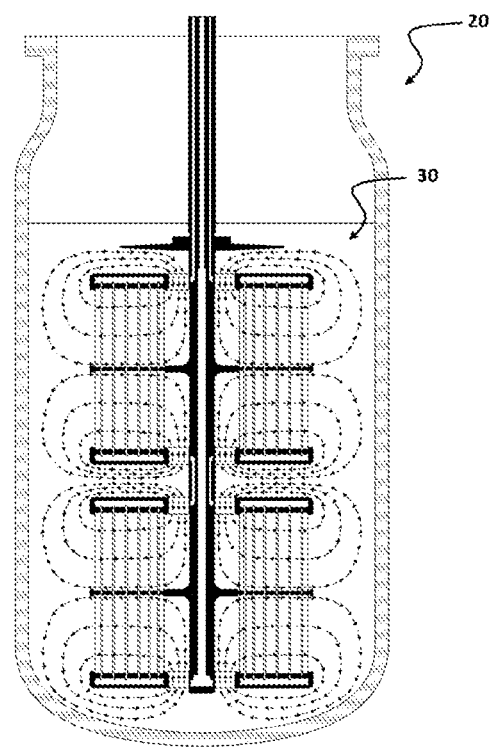
FIG. 13 is a schematic front view of a reactor according to the invention with two gassing units connected in series according to the invention, including a possible convective flow profile.

FIG. 13 shows a possible flow profile of a reactor 20 equipped with two gassing units 30 connected in series. The result is a uniform convection of the process liquid both over the entire reactor area and within the series-connected gassing unit 30.

Figure 14:
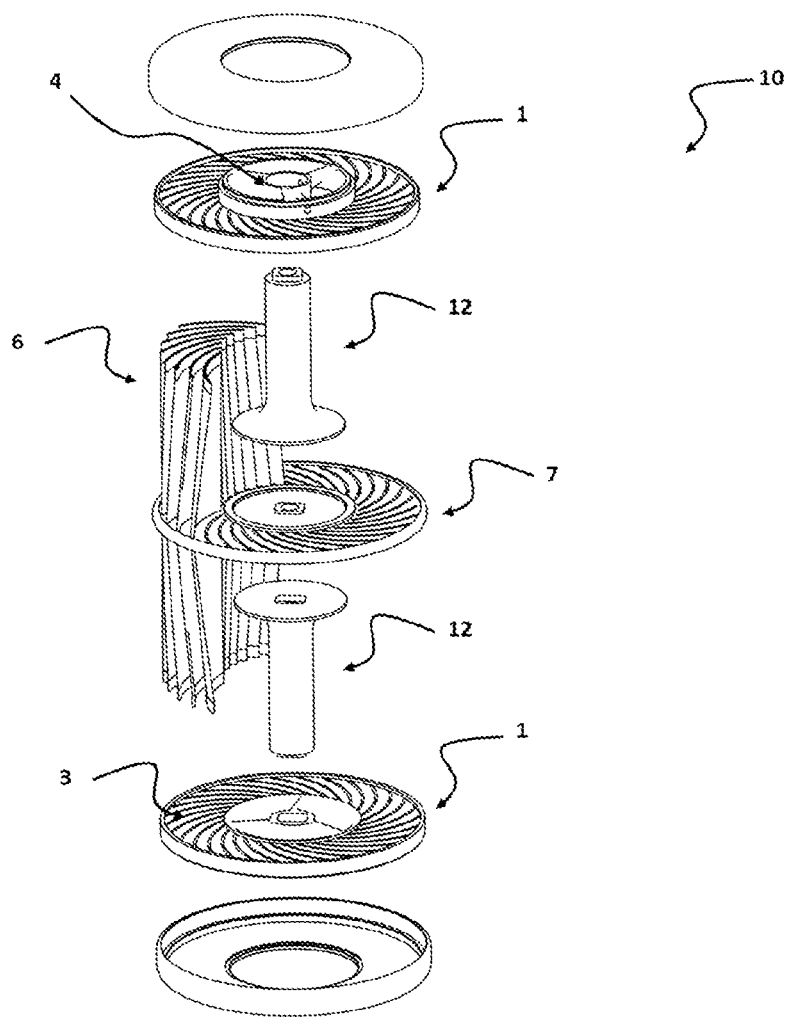
FIG. 14 is a schematic exploded view of a gassing unit according to the invention.

FIG. 14 shows an exploded view of a gas supply unit 10 according to the invention. The gas supply unit 10 can, for example, be driven and supplied with process gas by a hollow shaft (not shown in this figure), which is connected to the gas receiving chamber 1 at the receptacle 4. The shaft both provides the mechanical power to the unit and transports the process gas to the gas receiving chamber 1. The individual hollow fiber membranes 6 are arranged on the gas receiving chamber 1 so that they extend into the inner gas receiving chamber 11. The hollow fiber membranes are thus supplied with process gas through the inner gas receiving chamber 11, which is conducted through the hollow fibers of the diffusion membranes 6 into the other (lower) gas receiving chamber 1. The process gas can pass from the hollow fibers of the diffusion membranes 6 into the process liquid, thus supplying the liquid with process gas. Both gas receiving chambers 1 are thereby additionally connected to each other via a mechanical support 12. This support 12 can be used for other technical functions in addition to purely mechanical support. In this embodiment, the second (lower) gas receiving chamber 1 also comprises a receptacle 4 for process gas. The process gas that has not diffused out of the membranes 6 is led out of the gassing unit 10 again via the hollow shaft of the mechanical support 12. In this embodiment, the gassing unit 10 is thus operated in a "cross-flow" mode. In general, the process gas can be fed in and out via a central hollow shaft in the mechanical support 12, which is connected to the outer periphery of one or both gas receiving chambers 1 via receptacles 4. In particular, the latter embodiment can reduce the number of necessary connection points and contribute to a compact design. In addition, it can be seen in this embodiment that the individual gas receiving chambers 1 can be protected above and below by cover plates.

The invention claimed is:

1. A gassing unit for bubble-free introduction of a process gas into a liquid located in a reactor, characterized in that the gassing unit at least comprises:
    a first gas receiving chamber and, spaced therefrom, a second gas receiving chamber for receiving a process gas, the two gas receiving chambers being connected to one another via at least two two-dimensional, gas-conducting diffusion membranes in a form of hollow fibers spaced apart from one another and at least partially fixed to one another;
    a receptacle for a gas supply on at least one of the gas receiving chambers;
    a receptacle for a shaft on at least one of the gas receiving chambers;

wherein the gassing unit for gassing the liquid in the reactor is supplied with process gas via the receptacle for the gas supply, set into a rotational movement via the receptacle for the shaft, and forms a convection flow within the reactor via the rotational movement of the gassing unit in the liquid.

2. The gassing unit according to claim 1, wherein the projections of the diffusion membranes onto the gas receiving chambers have a circular arc geometry.

3. The gassing unit according to claim 1, wherein the receptacle for the gas supply and the receptacle for the shaft (9) are arranged at only one gas receiving chamber.

4. The gassing unit according to claim 1, wherein the two gas receiving chambers are each of cylindrical shape and are interconnected via one or more mechanical supports.

5. The gassing unit according to claim 4, wherein at least one retaining disk is arranged between the two gas receiving chambers on the mechanical support, which is set up to mechanically retain the diffusion membranes.

6. The gassing unit according to claim 4, wherein the mechanical support is adapted to transport process gas from the gas receiving chambers.

7. The gassing unit according to claim 1, wherein the area ratio of total hollow fiber cross-sectional area to the cross-sectional area of the gas receiving chamber is greater than or equal to 5% and less than or equal to 45%.

8. The gassing unit according to claim 1, wherein the packing density of the diffusion membranes relative to the volume of the gassing unit, ex-pressed as the surface area of the hollow fibers divided by the volume of the gassing unit, is greater than or equal to $0.1$ $cm^{-1}$ and less than or equal to $7.5$ $cm^{-1}$.

9. Method-A method for gassing a process liquid within a reactor, comprising providing a process liquid within a reactor and gassing the process liquid via a gassing unit according to claim 1.

10. The method of claim 9, wherein a rotational speed of a membrane surface at an outermost edge of the gassing unit is greater than or equal to 0.1 m/s and less than or equal to 5 m/s.

11. A gas-liquid reactor at least comprising an outer reactor shell, a drive unit, a gas supply and a gassing unit, the gassing unit including:
a first gas receiving chamber and, spaced therefrom, a second gas receiving chamber for receiving a process gas, the two gas receiving chambers being connected to one another via at least two two-dimensional, gas-conducting diffusion membranes in the form of hollow fibers spaced apart from one another and at least partially fixed to one another;
a receptacle for a gas supply on at least one of the gas receiving chambers;
a receptacle for a shaft on at least one of the gas receiving chambers;
wherein the gassing unit for gassing the liquid in the reactor is supplied with process gas via the receptacle for the gas supply, is set into a rotational movement via the receptacle for the shaft and forms a convection flow within the reactor via the rotational movement of the gassing unit in the liquid.

12. The gas-liquid reactor according to claim 11, wherein the reactor does not comprise a stirring unit other than the gassing unit.

13. The gas-liquid reactor according to claim 12, wherein at least one flow breaker is arranged between the reactor shell and the gas receiving chambers.

14. A method of supplying process gases to biological cultures suspended in a process solution or adhering to the reactor interior or to the gassing unit comprising:
providing a gas-liquid reactor comprising an outer reactor shell, a drive unit, a gas supply and a gassing unit, the gassing unit including:
a first gas receiving chamber and, spaced therefrom, a second gas receiving chamber for receiving a process gas, the two gas receiving chambers being connected to one another via at least two two-dimensional, gas-conducting diffusion membranes in the form of hollow fibers spaced apart from one another and at least partially fixed to one another;
a receptacle for a gas supply on at least one of the gas receiving chambers;
a receptacle for a shaft on at least one of the gas receiving chambers;
wherein the gassing unit for gassing the liquid in the reactor is supplied with process gas via the receptacle for the gas supply, is set into a rotational movement via the receptacle for the shaft and forms a convection flow within the reactor via the rotational movement of the gassing unit in the liquid, and
supplying process gases to the biological cultures.

15. The method of claim 14, wherein the biological cultures are adapted to produce foam-forming substances.

* * * * *